(12) United States Patent
Sharpe et al.

(10) Patent No.: US 8,263,600 B2
(45) Date of Patent: Sep. 11, 2012

(54) ANTIFUNGAL COMPOSITION WITH ENHANCED BIOAVAILABILITY

(75) Inventors: Stefan Sharpe, Jersey City, NJ (US); Joel Sequeira, Edison, NJ (US); David Harris, New Providence, NJ (US); Shashank Mahashabde, Kendall Park, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/161,097

(22) Filed: Jun. 15, 2011

(65) Prior Publication Data

US 2011/0244004 A1 Oct. 6, 2011

Related U.S. Application Data

(63) Continuation of application No. 10/114,612, filed on Apr. 1, 2002, now abandoned.

(60) Provisional application No. 60/281,139, filed on Apr. 3, 2001.

(51) Int. Cl.
*A61K 31/497* (2006.01)

(52) U.S. Cl. ............... 514/254.05; 514/384; 424/489

(58) Field of Classification Search .............. None
See application file for complete search history.

(56) References Cited

U.S. PATENT DOCUMENTS

| | | | | |
|---|---|---|---|---|
| 4,788,220 | A | | 11/1988 | Mody et al. |
| 5,145,684 | A | * | 9/1992 | Liversidge et al. ........... 424/489 |
| 5,318,767 | A | | 6/1994 | Liversidge et al. |
| 5,374,659 | A | * | 12/1994 | Gowan, Jr. .................... 514/557 |
| 5,399,363 | A | | 3/1995 | Liversidge et al. |
| 5,451,393 | A | | 9/1995 | Liversidge et al. |
| 5,494,683 | A | | 2/1996 | Liversidge et al. |
| 5,552,160 | A | | 9/1996 | Liversidge et al. |
| 5,580,579 | A | * | 12/1996 | Ruddy et al. .................. 424/489 |
| 5,645,856 | A | | 7/1997 | Lacy et al. |
| 5,661,151 | A | | 8/1997 | Saksena et al. |
| 5,834,472 | A | * | 11/1998 | Sangekar et al. ........ 514/254.07 |
| 5,846,971 | A | | 12/1998 | Sangekar et al. |
| 5,922,709 | A | | 7/1999 | Okada et al. |
| 2001/0036966 | A1 | | 11/2001 | Yasueda et al. |
| 2005/0048126 | A1 | | 3/2005 | Rabinow et al. |

FOREIGN PATENT DOCUMENTS

| | | |
|---|---|---|
| EP | 0499299 A2 | 8/1992 |
| WO | WO-95/17407 A1 | 6/1995 |
| WO | WO-99/61001 A1 | 12/1999 |

OTHER PUBLICATIONS

Zatz et al. "Viscosity—Imparting Agents in Disperse Systems" from Pharmaceutical Dosage Forms: Disperse Systems, vol. 1, 2nd edition, p. 287-290, 1996.*
Antal et al., "Comparative bioavailability of two medroxyprogesterone acetate suspensions," International Journal of Pharmaceutics, 54: 33-39 (1989).

Cacciapuoti et al., "In Vitro and in Vivo Activities of SCH 56592 (Posaconazole), a New Triazole Antifungal Agent, against *Aspergillus* and *Candida*," Antimicrobial Agents and Chemotherapy, 44: 2017-2022 (2000).
Connolly et al., "Comparison of a new triazole posaconazole, with itraconazole and amphotericin B for treatment of histoplasmosis following pulmonary challenge in immunocompromised mice," Antimicrobial Agents and Chemotherapy, 44(10): 2604-2608 (2002).
Excerpt from New Drug Application File for NOXAFIL® (posaconazole) Oral Suspension, "Posaconazole NDA Amendment: Revised Particle Size Specification" Made public by submission with response to Office Action filed in U.S. Appl. No. 10/114,612 on Jan. 25, 2006.
Ezzet et al., "The pharmacokinetics of posaconazole in neutropenic oncology patients," Abstract from the 41st Annual Meeting of the Interscience Conference on Antimicrobial Agents and Chemotherapy; Chicago, Illinois, USA; Sep. 22-25, 2001, 41:4 (2001).
FDA-approved labeling for NOXAFIL® (posaconazole) Oral Suspension (Oct. 2006), as submitted with response to Office Action filed in U.S. Appl. No. 10/114,612 on Jul. 13, 2007.
Kim et al., "High-Performance Liquid Chromatographic Analysis of the Anti-Fungal Agent SCH 56592 in Dog Serum," Journal of Chromatography B, 738: 93-98 (2000).
Kwon et al., "Posaconazole: a new broad-spectrum antifungal agent," Expert Opinion Pharmacotherapy, 8(8): 1167-1178 (2007).
Mellinghoff et al., "Use of posaconazole (SCH56592) for treatment of invasive fungal infections refractory to standard antifungal therapy," (Abstract from the 42nd Annual Meeting of the American Society of Hematology; San Francisco, California, USA; Dec. 1-5, 2000), Blood, 96(11 Part 2):341b (2000).

(Continued)

*Primary Examiner* — Nissa Westerberg
(74) *Attorney, Agent, or Firm* — Covington & Burling LLP; Paul J. Berman; Natalie M. Derzko (57) ABSTRACT

A liquid suspension comprising an antifungally effective amount of the micronized compound represented by the chemical structural formula I:

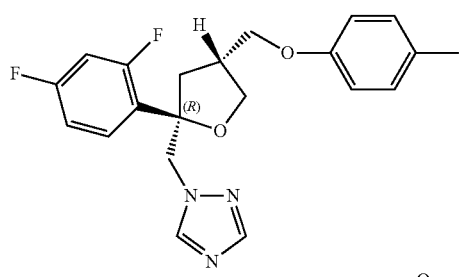

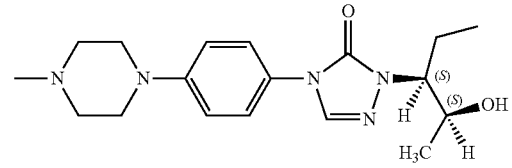

at least one thickening agent, a non-ionic surfactant, and a pharmaceutically acceptable liquid carrier is disclosed.

5 Claims, 1 Drawing Sheet

OTHER PUBLICATIONS

Nomeir, Antimicrobial Agents and Chemotherapy, 44(3):727-731 (2000).

"The Merck Manual of Diagnosis and Therapy," Merck Research Laboratories, Sixteenth Edition, 1992, 159-161.

Petraitiene et al., "Correlation between serum galactomannan concentration and antifungal efficacy of posaconazole (SCH 56592) in treatment and prevention of invasive pulmonary aspergillosis in persistently neutropenic rabbits," Abstract from the 40th Annual Meeting of the Interscience Conference on Antimicrobial Agents and Chemotherapy; Toronto, Ontario, Canada; Sep. 17-20, 2000, 40:380-381 (2000).

Pitisuttithum et al., "Activity of posaconazole in the treatment of central nervous system fungal infections" J. of Antimicrobial Chemotherapy, 56: 745-755 (2005).

Saha, Eur. J. of Pharmaceutics and Biopharmaceutics, 50:403-411 (2000).

Saksena et al., "Concise asymmetric routes to 2,2,4-trisubstituted tetrahydrofurans via chiral titanium imide enolates: key intermediates towards synthesis of highly active azole antifungals SCH 51048 and SCH 56692," Tetrahedron Letters, 37: 5657-5660 (1996).

Skiest et al., "Treatment of azole-refractory candidiasis in HIV disease," Abstract from the 39th Annual Meeting of the Interscience Conference on Antimicrobial Agents and Chemotherapy; San Francisco, California, USA; Sep. 26-29, 1999, 39:489 (1999).

Timmins et al., "Development of a Glyburide-Metformin Fixed Combination Tablet with Optimized Glyburide Particle Size," Drug Development Research, 66: 25-35 (2006).

Zatz et al., "Viscosity-Imparting Agnets in Disperse Systems" from Pharmaceutical Dosage Forms: Disperse Systems vol. 1, Second Edition, p. 287-290, 1996.

* cited by examiner

ANTIFUNGAL COMPOSITION WITH ENHANCED BIOAVAILABILITY

BACKGROUND OF THE INVENTION

This invention relates to stable, liquid suspensions containing an antifungally effective amount of the micronized compound represented by the chemical structural formula I:

at least one thickening agent, a non-ionic surfactant, and a pharmaceutically acceptable liquid carrier, and methods of using the suspensions to treat or prevent fungal infections U.S. Pat. No. 5,661,151 discloses the compound of formula I and its potent antifungal activity against a broad range of fungi such as *Aspergillis, Candida, Cryptococcus, Fusarium*, and other opportunistic fungi.

U.S. Pat. Nos. 5,834,472 and 5,846,971, disclose oral pharmaceutical capsule compositions of the compound of structural formula I coated onto inert beads together with a binder. However, the compound of structural formula I is highly lipophilic, and has an extremely low water solubility. Thus, aqueous compositions of the compound of structural formula I were found to have reduced anti-fungal activity and/or bioavailability, presumably due to the extremely low water solubility of the compound. Accordingly, a need exists for an oral pharmaceutical composition of the compound of structural formula I that has enhanced bioavailability and improved stability characteristics

SUMMARY OF THE INVENTION

We have found pharmaceutical compositions, in the form of liquid suspension, suitable for oral administration comprising micronized particles of posaconazole, the compound having the chemical structural formula I at least one thickening agent, a non-ionic surfactant, and a pharmaceutically acceptable liquid carrier that provides significant advantages over the prior art.

Advantages of the liquid suspensions of the present invention include improved homogeneity of the suspension and ease of dispersibility of the suspension. The solids that settle in the liquid suspension of the present invention do not form a solid cake that is difficult to re-disperse. There is virtually no sedimentation of the solids in the unreconstituted liquid suspension of this invention for a period of at least three days. This surprising feature ensures that a patient having a fungal infection taking the liquid suspensions of the present invention will receive an antifungally effective amount of posaconazole. The liquid suspensions of the present invention have a longer shelf life. Additionally, the liquid suspension, upon reconstitution, provide substantially the same antifungally effective amount posaconazole as the initially prepared suspension. These features of the liquid suspensions of the present invention provide benefits to pharmacies, pharmacists, doctors and patients having fungal infections.

Accordingly, the present invention provides a liquid suspension comprising micronized posaconazole, having the chemical structural formula I:

at least one thickening agent, a non-ionic surfactant, and a pharmaceutically acceptable liquid carrier.

This invention also provides a liquid suspension comprising an antifungally effective amount of micronized posaconazole having the chemical structural formula I:

an effective amount of at least one thickening agent, an amount of a buffer system effective to maintain the pH of the system in the range of about 4.0 to about 6.0, an effective amount of a non-ionic surfactant, and a pharmaceutically acceptable liquid carrier.

This invention further provides a liquid suspension comprising an antifungally effective amount of micronized posaconazole having the chemical structural formula I:

wherein the micronized compound has a mean particle size in the range of about 1200 nm to about 1600 nm, an effective amount of polyoxyethylene derivatives of sorbitan esters of saturated or unsaturated $C_{12}$ to $C_{18}$ acids, an effective amount of a buffer system sufficient to maintain a pH in the range of about 4.0 to about 6.0, an effective amount of a combination of two thickening agents, wherein one is a liquid sugar, and a pharmaceutically acceptable liquid carrier.

BRIEF DESCRIPTION OF THE FIGURES

FIGS. 1 & 2 graphically display the mean plasma concentration time profiles of posaconazole tablets and of the liquid suspension of Example 1 of the present invention. FIG. 1 is a linear:linear graphic profile of the plasma concentration (ng/ml) of the compound of formula I versus time (hours) after administration of the following four Treatments A-D: a single of 2×100 mg of the compound of formula I in the tablet co-precipitate formulation of U.S. Pat. No. 5,834,472 with a standardized high-fat breakfast—Treatment D and. symbol -●-; a 200 mg of the compound of formula I in the oral suspension of this invention (5 ml) following a 10-hr. fast— Treatment A and. symbol -0-; a 200 mg of the compound of formula I in the oral suspension of this invention (5 ml) with a standardized high-fat breakfast—Treatment B and. symbol -Δ-; and a 200 mg of the compound of formula I in the oral suspension of this invention (5 ml) with a standardized non-fat breakfast—Treatment C and. symbol-□-.

DETAILED DESCRIPTION OF THE INVENTION

The present invention provides a stable suspension of micronized particles of the antifungal compound posaconazole in a pharmaceutically acceptable liquid carrier. The suspension of the present invention is stable to settling without sedimentation when stored undisturbed for more than three days at 25° C. (See Table 1 below).

Table 2 below shows that the liquid suspension formulations of this invention are stable in that the concentration of posaconazole in the suspension is substantially the same (±2%) compared to the initial concentration (as measured by HPLC) for periods of up to 12 months.

We have also found that the stable suspension of the present invention has a remarkably higher (23-36% increase) bioavailability compared to an optimized oral tablet of micronized particles of posaconazole when each is administered to subjects concurrently with a high fat breakfast. See Tables 3 and 4 and FIGS. 1 &2

One aspect of the present invention is to provide a pharmaceutical composition that contains micronized particles of posaconazole in combination with a non-ionic surfactant, such as a sorbitan ester and at least one thickening agent, preferably a combination of xanthan gum and a liquid sugar, that are easily dispersible in a pharmaceutically acceptable liquid carrier such as purified water. The pharmaceutical composition provides a stabilized suspension that does not settle for at least three days, thus ensuring that patients will get an effective dose of posaconazole. Another feature of the stabilized suspension of the present invention is that it is useful in treating patients with HIV-1 infections with oral thrush without posaconazole precipitating out of solution. Another aspect of the present invention is that the suspension of the present invention avoids formation of solid cakes which are difficult to disperse.

The compound of formula I used in the suspensions of the present invention is available from Schering Corporation, Kenilworth, N.J., and has been prepared according to Examples 24 and 32 of U.S. Pat. No. 5,661,151 and WO 95/17407.

Micron-sized particles of posaconazole preferably have a mean particle size range of about 1000 nanometers (nm) to about 1800 nm, preferably about 1200 nm to about 1600 nm, and most preferably about 1400 nm. This particle size can be obtained either by the final step during the manufacture of the antifungal compound of formula I or by the use of conventional micronizing techniques after the conventional crystallization procedure(s).

The preferred micronizing technique that is employed to micronize the posaconazole to the desired mean particle size range is microfluidization. Microfluidization is an alternative to traditional homogenization that utilizes the collision of two product streams at high pressures to produce a much more uniform particle size distribution (according to Microfluidics International Co.) and smaller average particle size of about 1200 nm to 1600 nm. The process and equipment used in microfluidization are described in U.S. Pat. No. 4,533,254.

The micronized posaconazole of the present invention may also be present in crystalline form. It is preferably substantially chemically and optically pure, and it contains less than about 10% of its optical isomers, enantiomers or other diastereomers. It may be 99% of the optically pure the levorotatory or dextrarotatory isomer. This optically pure compound of chemical structure I should avoid many of the untoward side effects of a mixture of other optical isomers.

Posaconazole liquid suspension is employed in the composition in antifungally amounts effective to control the fungi of interest. Such antifungally effective amounts can range from about 10 mg/ml to about 100 mg/ml concentration of the liquid suspension formulations of the present invention, more preferably from about 20 mg/ml to about 60 mg/ml, and most preferably about 40 mg/ml of the compound of formula I.

The present invention also provides for a method of treating and/or preventing fungal infection in a mammal comprising administering to the mammal an amount of the liquid suspension containing the micronized posaconazole in an amount effective for treating and/or preventing such fungal infection. Antifungally effective amounts of liquid suspensions of present invention containing 40 mg/ml of the compound of formula I is administered orally in the doses of 5 ml—containing 200 mg of formula I—three times a day (TID) or four times a day (QID)—or 10 ml—containing 400 mg of the compound of formula 1—twice a day (BID). Of course, the attending clinician may change the dose and dosing regimen in view of the age, health, and sex of the patient as well as the severity of the fungal infection.

The following terms are used to describe the present pharmaceutical compositions, ingredients that may be employed in its formulation and methods for assessing the compound's bioactivity or bioavailability.

Non-ionic surfactant refers to a surfactant which lacks a net ionic charge and does not dissociate to an appreciable extent in aqueous media. The properties of non-ionic surfactants are largely dependent upon the proportions of the hydrophilic and hydrophobic groups in the molecule. Hydrophilic groups include the oxyethylene group ($-OCH_2CH_2-$) and the hydroxy group. By varying the number of these groups in a hydrophobic molecule, such as an ester of a fatty acid, substances are obtained which range from strongly hydrophobic and water insoluble compounds, such as glyceryl monostearate, to strongly hydrophilic and water-soluble compounds, such as the macrogols. Between these two extremes types include those in which the proportions of the hydrophilic and hydrophobic groups are more evenly balanced, such as the macrogol esters and ethers and sorbitan derivatives. Suitable non-ionic surfactants may be found in Martindale, The Extra Pharmacopoeia, 28th Edition, 1982, The Pharmaceutical Press, London, Great Britain, pp. 370 to 379.

Such suitable non-ionic surfactants include block copolymers of ethylene oxide and propylene oxide, glycol or glyceryl esters of saturated or unsaturated $C_8$ to $C_{20}$ acids, preferably, polyoxyethylene esters of saturated or unsaturated $C_8$ to $C_{20}$ acids, polyoxyethylene ethers of saturated or unsaturated $C_8$ to $C_{20}$ acids, and polyvinylalcohols or sorbitan esters of saturated or unsaturated $C_{10}$ to $C_{20}$ acids. Preferably, the non-ionic surfactant is a sorbitan ester of a saturated or unsaturated $C_{10}$ to $C_{20}$ acid, and more preferably the sorbitan ester is a fatty acid ester of sorbitan selected from sorbitan monolaurate, sorbitan monooleate, sorbitan sesquioleate, sorbitan trioleate, sorbitan monopalmitate, sorbitan monostearate and sorbitan tristearate, or mixtures thereof.

Suitable sorbitan esters include, e.g. Polysorbate 20, Polysorbate 40, Polysorbate 60, Polysorbate 65, Polysorbate 80, Polysorbate 85, Sorbitan Monolaurate, Sorbitan Monooleate, Sorbitan Monopalmitate, Sorbitan Monostearate, Sorbitan Sesquioleate, Sorbitan Trioleate and Sorbitan Tristearate. The most preferred non-ionic surfactant is Polysorbate 80, available from ICI Americas under the tradename Tween 80 which is a mixture of oleate esters of sorbitol and sorbitol anhydrides, consisting predominantly of the monoester, condensed with approximately 20 moles of ethylene oxide.

Suitable block copolymers of ethylene oxide and propylene oxide generically called "Poloxamers" and include those represented by the following chemical structure I:

wherein a is an integer ranging from about 10 to about 110, preferably from about 12 to 101; more preferably from about 12 to 80; and b is an integer ranging from about 20 to about 60, more preferably from about 20 to about 56; also from about 20 to 27.

Suitable glycol and glyceryl esters of fatty acids include glyceryl monooleate and similar water soluble derivatives;

Suitable polyoxyethylene esters of fatty acids (macrogol esters) include polyoxyethylene castor oil and hydrogenated castor oil derivatives;

Suitable polyoxyethylene ethers of fatty acids (macrogol ethers) include Cetomacrogel 1000, Lauromacrogols (a series of lauryl ethers of macrogols of differing chain lengths), e.g. Laureth 4, Laureth 9 and Lauromacrogol 400.

The effective amount of non-ionic surfactant in the composition can range from about 5 mg/ml to about 50 mg/ml concentration of the formulation, more preferably from about 5 mg/ml to about 25 mg/ml, and most preferably 10 mg/ml.

Thickening agents found suitable in the present invention include any commercially available agent useful for such purpose. Xanthan gum, liquid sugars, starches, celluloses and mixtures thereof are preferred thickening agents. More preferred is a combination of xanthan gum and a liquid sugar and, most preferred is a combination of xanthan gum, NF and glucose, NF. Preferably, the xanthan gum is present in an amount of about 1 mg/ml to about 5 mg/ml, and more preferably the xanthan gum is present in an amount of about 3 mg/ml. Preferably, the glucose NF is present in an amount of about 200 to about 500 mg/ml, and more preferably about 350 mg/ml. The effective amount of thickening agent of the present invention may be about 1 to about 500 mg/ml, more preferably about 200 to about 500 mg/ml, most preferably about 353 mg/ml. The thickening agents of the present invention facilitate suspension of the formulation after constitution with minimum agitation and prevent rapid settling and caking of the suspension over time.

Pharmaceutically acceptable carriers include those well known in the art, including purified water USP, liquid glucose, NF, and anhydrous glycerol. Most preferred is purified water USP and liquid glucose, NF. The pharmaceutically acceptable carrier may be present in an amount of about 10 to about 500 mg/ml, more preferably about 200 mg/ml to about 400 mg/ml, most preferably about 350 mg/ml.

The buffer systems suitable for the formulations of the present invention are those which maintain the pH of the liquid suspension in the range of about 4 to about 6, preferably in the 4.5 to 5.0, and most preferably about 4.5. The use of a buffer system of sodium citrate, USP and citric acid, USP, is preferred. Other suitable buffer systems may be used to maintain the desired pH range of 4 to 6. The buffering agents may be present in a concentration of about 0.4 to about 1.5 mg/ml, more preferably about 0.7 to about 1.5 mg/ml, most preferably about 1.1 mg/ml.

Anti-foaming agents found suitable in the present invention include any commercially available agent useful for such purpose including the methylated linear siloxsane polymers end blocked with trimethylsiloxyl units such as dimethicone and simethicone, as well as mixtures of dimethicone with an average chain length of 200 to 250 dimethylsiloxane units and silica gel. The effective amount of anti-foaming agents is an amount sufficient to provide a concentration of about 2 mg/ml to about 4 mg/ml, preferably about 3 mg/ml.

The water soluble preservatives found useful in present invention include sodium benzoate, sodium citrate and benzalkonium chloride as well as other pharmaceutically acceptable water soluble preservatives. Use of sodium benzoate as a preservative is preferred. The effective amount of the water soluble preservative is an amount sufficient to provide a concentration of about 0.5 mg/ml to about 3 mg/ml, most preferably about 2 mg/ml.

The opacifier agents found suitable in the present invention include pharmaceutically acceptable metal oxides, especially titanium dioxide. The effective amount of the opacifier agent is an amount sufficient to provide a concentration of about 2 mg/ml to about 6 mg/ml, most preferably about 4 mg/ml.

Typical flavoring agents are those that are approved by FDA for use in sweetened pharmaceuticals, foods, candies, beverages and the like; these materials impart flavors such as grape, cherry, citrus, peach, strawberry, bubble gum, peppermint and many others. The effective amount of the flavoring agents is an amount sufficient to provide a concentration of about 0.01 mg/ml to about 6 mg/ml, more preferably about 5 mg/ml.

The following examples describe compositions of the present invention containing posaconazole, but they are not to be interpreted as limiting the scope of the claims.

| Ingredient | Concentration Range (mg/ml) |
| --- | --- |
| Posaconazole (micronized) | 10-100 |
| Polysorbate 80 | 5-50 |
| Sodium Citrate, USP, Monohydrate | 0.4-0.8 |
| Citric Acid, USP, Monohydrate | 0.36-0.6 |
| Simethicone, USP | 2-4 |
| Xanthan Gum, NF | 1-5 |
| Sodium Benzoate, NF | 0.5-3 |
| Liquid Glucose, NF | 200-500 |
| Glycerin, USP | 50-150 |
| Artificial Cherry Flavor | 2-10 |
| Titanium Dioxide | 2-6 |
| Purified Water, USP q.s. ad | — |

The above ranges of ingredients may be varied as is evident to one skilled in the art. Specific examples of a composition within the scope of the invention is set forth below.

EXAMPLE 1

| Ingredient | Concentration (mg/ml) |
| --- | --- |
| Posaconazole (micronized) | 40 |
| Polysorbate 80 | 10 |
| Sodium Citrate, USP, Monohydrate | 0.6 |
| Citric Acid, USP, Monohydrate | 0.48 |
| Simethicone, USP | 3 |
| Xanthan Gum, NF | 3 |
| Sodium Benzoate, NF | 2 |
| Liquid Glucose, NF | 350 |
| Glycerin, USP | 100 |
| Artificial Cherry Flavor | 5 |
| Titanium Dioxide | 4 |
| Purified Water, USP q.s. ad | 1 ml |

This example is prepared as follows: charge approximately 5% of the final batch volume of purified water at 20±3° C. to a suitable vessel equipped with a mixer propeller. Add 40% of the polysorbate 80 to the purified water in step 1 and mix until dissolved. Add 40% of the simethicone and mix until it is dispersed. Recirculate the mixture in step 3 through a Microfluidizer, operating at about 30,000±5000 psi for approximately 5 passes. Add approximately 7% of the final batch volume of purified water at about 20±3° C., and mix for approximately five minutes. Add the Posaconazole to the vessel in step 5 with constant mixing. Continue mixing until it is fully dispersed. Recirculate the suspension portion from step 6 through a Microfluidizer, operating at a pressure of about 30,000±5,000 psi. Process the concentrate until the median of the particles shows a particle size of about 1.4±0.2 μm, when measured via laser diffraction techniques that are known in the art.

When the particle size has been achieved, pass the suspension through the microfluidizer and collect in a suitable sized vessel. Add approximately 8-10% of the final batch volume of purified water (at 20±3° C.) to the feed vessel, and pass through the microfluidizer operating at approximately 30,000 psi. Collect the rinse in the vessel containing the concentrate. Add approximately 22% of the final batch volume of purified water (20±3° C.) to the vessel with the concentrate, and mix for approximately five (5) minutes. Add the remainder of the polysorbate 80 and simethicone, and mix for approximately five (5) minutes.

Add the sodium benzoate, sodium citrate and citric acid and mix for approximately five (5) minutes. Add the xanthan gum slowly with constant mixing. Continue to mix after addition of the xanthan gum. Allow the xanthan gum to hydrate without mixing for 30 minutes. Add the glycerin with constant mixing. Add the liquid glucose slowly with constant mixing. Mix for five minutes or until it is dissolved. Add the titanium dioxide and mix using a suitable homogenizer until that ingredient is fully dispersed. Add the artificial cherry flavor, and mix for approximately five minutes. Add purified water at 20±3° C., and qs up to a final volume, and mix until a uniform suspension is attained. Collect approximately 20 ml sample for pH measurement and physical observation of the suspension. The pH of the suspension of Example 1 was 5.0.

EXAMPLE 2

Example 2 is another example of a formulation within the scope of the present invention prepared using the procedure of Example 1 and has a pH of 4.5.

| Ingredient | Concentration (mg/ml) |
| --- | --- |
| Posaconazole (micronized) | 40 |
| Polysorbate 80 | 10 |
| Sodium Citrate, USP, Monohydrate | 0.6 |
| Citric Acid, USP, Monohydrate | 1.5 |
| Simethicone, USP | 3 |
| Xanthan Gum, NF | 3 |
| Sodium Benzoate, NF | 2 |
| Liquid Glucose, NF | 350 |
| Glycerin, USP | 100 |
| Artificial Cherry Flavor | 5 |
| Titanium Dioxide | 4 |
| Purified Water, USP q.s. ad | 1 ml |

The rate of sedimentation of the liquid suspension of the present invention was determined as set forth below.

TABLE 1

Posaconazole Oral Suspension 40 mg/ml
Rate of Sedimentation

| Bottle Number | Time | Posaconazole mg/ml | % Label Strength | Sodium Benzoate mg/ml | % Label Strength |
| --- | --- | --- | --- | --- | --- |
| 1 | 0 min | 39.9 | 99.8 | 2.00 | 100 |
| 1 | 5 min | 40.0 | 100 | 1.99 | 99.5 |
| 1 | 10 min | 40.0 | 100 | 2.00 | 100 |
| 1 | 30 min | 40.0 | 100 | 2.00 | 100 |
| 1 | 60 min | 40.2 | 101 | 2.01 | 101 |
| 1 | 3 days | 40.2 | 101 | 2.02 | 101 |
| 2 | 0 min | 39.8 | 99.5 | 2.01 | 101 |
| 2 | 5 min | 39.9 | 99.8 | 2.00 | 100 |
| 2 | 10 min | 40.2 | 101 | 2.01 | 101 |
| 2 | 30 min | 39.8 | 99.5 | 1.99 | 99.5 |
| 2 | 60 min | 40.2 | 101 | 2.02 | 101 |
| 2 | 3 days | 40.1 | 100 | 2.01 | 101 |

Two bottles containing the suspension of the present invention were shaken and left to rest. The bottles were then sampled immediately (time zero), then after 5 minutes, 10 minutes, 30 minutes, 60 minutes and after 72 hours (three days) post shaking. The levels of posaconazole and of the preservative (Sodium Benzoate) in these samples were assayed by HPLC. HPLC methods of detection are well-known to one of skill in the art.

The results of the assay of the preservative and of the posaconazole remained consistent and did not change. These ranged from 39.8 to 40.2 mg/ml (99.5 to 101%) for the active and 1.99 to 2.02 mg/m: (99.5 to 101%) for the preservative, respectively. The results of this experiment are shown in Table 1 above.

The sodium benzoate was not expected to sediment. Surprisingly, the posaconazole was not sedimented after 3 days.

Thus, the compositions of the present invention have both ease of dispersibility and homogeneity as is evidenced by the stability of the samples in Table 1.

Next, accelerated homogeneity testing was performed on the liquid suspension of the present invention.

TABLE 2

Posaconazole Oral Suspension 40 mg/ml
Homogeneity

| Accelerated Condition | Time point | Posaconazole % Label Strength | Sodium Benzoate % Label Strength |
| --- | --- | --- | --- |
| Initial | Initial | 103; 102; 104 | 105; 102; 103 |
| 30 H (30° C./60% RH) | 3 Months | 103; 105; 104 | 103; 107; 105 |
| RH4 (40° C./75% RH) | 3 Months | 102; 104; 103 | 104; 106; 106 |
| 30 H | 6 Months | 102; 101; 102 | 103; 101; 102 |
| RH4 | 6 Months | 102; 102; 102 | 101; 101; 102 |
| 25 H | 12 Months | 104; 104; 104 | 101; 100; 100 |
| 25 H | 24 Months | 104; 104; 104 | 101; 101; 101 |

* Shaking and receiving the dose as per patient instruction.

These data (sedimentation rate experiment) were in agreement with the real time stability data (up to 6 months at 40° C./75% RH and up to 24 months at 25° C./60% RH) that are shown in Table 2. The assay homogeneity results, surprisingly, remained consistently homogenous and practically unchanged.

After 6 months at 40° C./75% RH the homogeneity results ranged from 40.7 to 40.8 mg/ml (101%) for the active and 2.01 to 2.03 mg/ml (101 to 102%) for preservative, respectively. These results were obtained regardless of the portion of the bottle assayed, i.e., top, or bottom of the bottle. Therefore, it can be concluded that the suspension was homogenous throughout the bottle even after relatively long exposure to accelerated stability conditions.

After 24 months at 25° C./60% RH the homogeneity results ranged from 41.5 to 41.6 mg/ml (104%) for the active and 2.01 mg/ml (101%) for the preservative, respectively. These results were obtained regardless of the portion of the bottle assayed, i.e., top or bottom of the bottle. Therefore, it can be concluded that the suspension was homogenous throughout the bottle even after long term (24 months) exposure to 25° C./60% RH.

Bioavailability is defined as the rate and extent to that the active drug ingredient or therapeutic moiety is absorbed into the systemic circulation from an administered dosage form as compared to a standard or control.

$C_{max}$ value is defined as the maximum concentration of the antifungal compound measured (i.e. "peak") in the plasma serum.

Formulations of the present invention have the advantage that they have an increased bioavailability and lower variability than previous formulations.

The relative bioavailability of the posaconazole oral suspension was compared to a solid dosage form of posaconazole in healthy subjects.

The first objective was to determine the relative bioavailability of posaconazole given as an oral suspension compared to an oral solid formulation when administered with a high-fat breakfast. The second objective was to determine the effect of high-fat and non-fat food relative to fasting conditions on the oral bioavailability of the compound of formula I when given as an oral suspension.

Twenty healthy subjects completed this randomized, open-label, 4-way crossover, single-dose bioavailability and food effect study of posaconazole. Subjects received each of the following four treatments separated by at least a 7 day washout period:

| | |
|---|---|
| Treatment A: | 200 mg of the compound of formula I in the oral suspension of this invention (5 ml) following a 10-hr. fast |
| Treatment B: | 200 mg of the compound of formula I in the oral suspension of this invention (5 ml) with a standardized high-fat breakfast |
| Treatment C: | 200 mg of the compound of formula I in the oral suspension of this invention (5 ml) with a standardized non-fat breakfast |
| Treatment D: | 2 × 100 mg of the compound of formula I in the tablets (co-precipitate formulation of U.S. Pat. No. 5,834,472 with a standardized high-fat breakfast |

Subjects were randomized to either remain fasted (Treatment A), to receive a standardized high fat breakfast (Treatment B or D) or a standardized non-fat breakfast (Treatment C). Meals were consumed in a 20-minute period prior to the morning drug administration and subjects received the appropriate treatment within 5 minute of completing the breakfast.

Blood samples (6 ml) were collected into heparinized tubes for each treatment immediately prior to dosing (0 hour) and at 0.5, 1, 1.5, 2, 3, 4, 5, 6, 8, 10, 12, 16, 24, 36, 48 and 72 hours after dosing. Blood was centrifuged at 4° C. and plasma stored at or below −20° C. until assayed. Plasma concentrations of posaconazole were assayed using a validated high performance liquid chromatographic assay with a LOQ of ng/ml.

Individual plasma concentration-time data were used for pharmacokinetic analysis using model-independent methods. The maximum concentration (Cmax) and time of maximum concentration (Tmax) were the observed values. The area under the plasma concentration-time curve from time zero to the final quantifiable sampling time [AUC(tf)] was calculated using the linear trapezoidal method and extrapolated to infinity (I) as follows:

$$AUC(I) = AUC(tf)\frac{C(tf)}{K}$$

where C(tf) is the estimated concentration determined from linear regression at time, if.

Total body clearance was calculated by the following:

$$CL=\text{Dose}/AUC(I)$$

The apparent volume of distribution (Vdarea/F) was calculated from the ratio of the total body clearance to the terminal phase rate constant (K).

Summary statistics were calculated for the plasma suspension formulation of the present invention compared to a prior art tablet formulation concentration-time data at each time point and the derived pharmacokinetic parameters. The original scale and log-transformed Cmax and AUC values were analyzed using an analysis of variance (ANOVA). The effects due to subject, phase and treatment were extracted.

Figure 1:
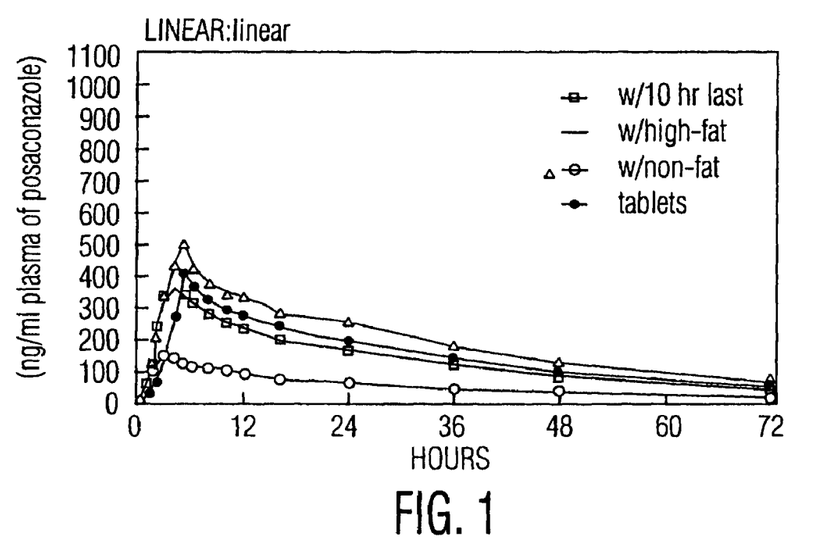
Figure 2:
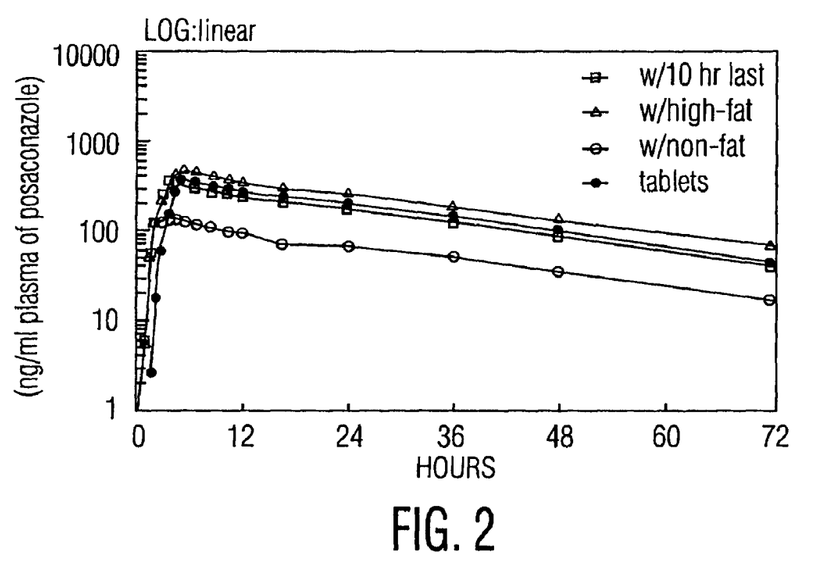
FIG. 2 is a log :linear graphic profile of the plasma concentration (ng/ml) of the compound of formula I versus time in hours for the data presented in FIG. 1.

The plasma concentration-time data and pharmacokinetic parameters for the compound of formula I are tabulated in Tables 3 & 4 and depicted graphically in FIGS. 1 & 2.

All subjects had 0-hour concentrations on Day 1 reported as below the LOQ (5 ng/ml) except for Subject 20 in Phases 3 and 4 who had quantifiable levels of posaconazole at 0-hour for Treatments B and A of 8.5 and 22.5 ng/ml, respectively. These levels are most likely due to a carry-over effect from accumulation from previous doses.

A summary of the mean[a] pharmacokinetic parameters are provided in the table below:

TABLE 3

| | | Tablet | | Suspension | | | | | |
|---|---|---|---|---|---|---|---|---|---|
| | | High Fat D | | 10 hr Fast A | | High Fat B | | Non-Fat C | |
| Parameter | Unit | Mean | % CV | Mean | % CV | Mean | % CV | Mean | % CV |
| Cmax | ng/ml | 413 | 33 | 132 | 50 | 512 | 34 | 378 | 43 |
| Tmax | Hr | 5.5 | 32 | 5.01 | 49 | 4.8 | 9 | 4.1 | 21 |
| AUC(tf) | ng-hr/ml | 10304 | 41 | 3553 | 36 | 13885 | 41 | 9511 | 38 |
| AUC(I) | ng-hr/ml | 11832 | 39 | 4179 | 31 | 15059 | 26 | 10753 | 35 |
| t½ | hr | 21.0 | 15 | 23.5 | 25 | 23.0 | 19 | 22.2 | 18 | a: Balanced means, n = 20 except for AUC(I) and t½, n = 15

Posaconazole was slowly absorbed; the mean Tmax values ranged from 4.1 to 5.5 hr. Posaconazole was slowly eliminated with a mean terminal t½ of about 22 hour which was independent of treatment. This study was conducted to evaluate the bioavailability of posaconazole oral suspension (Treatment B) compared to a tablet formulation (Treatment D), both given with a high-fat food. The results, based on log-transformed data, are shown below:

TABLE 4

| Parameter | Treatments Given After High Fat Breakfast | Geometric Mean | Relative Bioavailability (%)[b] | 90% Confidence Interval |
|---|---|---|---|---|
| Cmax | Suspension | 485 ng/ml | 123.3 | 104-146 |
| | Tablet | 394 ng/ml | | |
| AUC(tf)[a] | Suspension | 13141 ng · hr/ml | 136.5 | 119-156 |
| | Tablet | 9624 ng · hr/ml | | |

[a]AUC(tf) was used for statistical comparisons because it could be calculated for all treatments for all subjects.
[b]Suspension relative to tablet.

On average, the suspension formulation of the present invention resulted in a 23% increase in Cmax and a 36% increase in AUC(tf) compared to the tablet of the prior art.

The secondary objective of the study was to evaluate the effect of high fat food (Treatment B) and non-fat food (Treatment C) compared to fasting (Treatment A) on the oral bioavailability of posaconazole administered as an oral suspension. The results, based on log-transformed data, are shown below:

TABLE 5

| Parameter | Suspension Treatments | Geometric Mean | Relative Bioavailability (%)[a] | 90% Confidence Interval |
|---|---|---|---|---|
| Cmax (ng/ml) | High-Fat | 485 | 417 | 352-493 |
| | Non-Fat | 345 | 296 | 250-350 |
| | Fast | 116 | — | — |
| AUC(tf) (ng · hr/ml) | High-Fat | 13141 | 392 | 343-448 |
| | Non-Fat | 8857 | 264 | 231-302 |
| | Fast | 3352 | — | — |

[a]Expressed as a percent of Treatment A - Suspension/Fast.

A high fat breakfast produced a 4-fold increase in the bioavailability of posaconazole given in a suspension. This was consistent with results from a previous study where food significantly increased the bioavailability of posaconazole by 3-5-fold for both tablet and capsule formulations. The effect of a non-fat breakfast (Treatment C) compared to fasting (Treatment A) was less, with a 2.5-3-fold increase in bioavailability.

Many modifications and variations of this invention can be made without departing from its spirit and scope, as will be apparent to one skilled in the art. The specific embodiments described herein are offered by way of example only, and the invention is to be limited only by the terms of the appended claims along with the full scope of equivalents to which such claims are entitled.

We claim:

1. A liquid suspension comprising:
   40 mg/ml of a micronized compound represented by the chemical structural formula I:

wherein the micronized compound of formula I has a mean particle size of about 1800 nm;
   Polysorbate 80;
   an effective amount of a buffer system comprising sodium citrate and citric acid sufficient to maintain a pH in the range of about 4.0 to about 6.0;
   a combination of thickening agents comprising xanthan gum and liquid sugar; and
   a pharmaceutically acceptable liquid carrier comprising glycerin.

2. A liquid suspension comprising:
   40 mg/ml of a micronized compound represented by the chemical structural formula I:

wherein the micronized compound of formula I has a mean particle size of about 1000 nm to about 1800 nm;
   Polysorbate 80;
   an effective amount of a buffer system comprising sodium citrate and citric acid sufficient to maintain a pH in the range of about 4.0 to about 6.0;
   a combination of thickening agents comprising xanthan gum and liquid sugar; and
   a pharmaceutically acceptable liquid carrier comprising glycerin.

3. A liquid suspension comprising:

posaconazole (micronized), represented by the chemical structural formula I:

wherein the micronized compound of formula I has a mean particle size of about 1000 nm to about 1800 nm in an amount of about 40 mg/ml;

Polysorbate 80, in an amount between about 5 mg/ml and about 50 mg/ml;

sodium citrate, in an amount between about 0.4 and about 0.8 mg/ml;

citric acid, in an amount between about 0.36 and about 0.6 mg/ml;

simethicone, in an amount between about 2 mg/ml and about 4 mg/ml;

xanthan gum, in an amount between about 1 mg/ml and about 5 mg/ml;

sodium benzoate, in an amount between about 0.5 mg/ml and about 3 mg/ml;

liquid glucose, in an amount between about 200 mg/ml and about 500 mg/ml; and glycerin, in an amount between about 50 mg/ml and about 150 mg/ml.

4. The liquid suspension of claim 1, wherein the suspension further comprises purified water.

5. The liquid suspension of claim 1, wherein the suspension further comprises:

artificial cherry flavor, in an amount between about 2 mg/ml and about 10 mg/ml; and titanium dioxide, in an amount about 2 mg/ml and about 6 mg/ml.

\* \* \* \* \*